United States Patent [19]

Bugaut et al.

[11] 3,961,879

[45] June 8, 1976

[54] DYE COMPOSITION FOR KERATINIC FIBERS CONTAINING A PHENOL COUPLER

[75] Inventors: Andree Bugaut, Boulogne-sur-Seine; Monique Laudon, Gagny, both of France

[73] Assignee: L'Oreal, Paris, France

[22] Filed: June 24, 1974

[21] Appl. No.: 482,559

[30] Foreign Application Priority Data

June 22, 1973 Luxemburg............................ 67862

[52] U.S. Cl. .................................. 8/10.2; 8/10; 8/10.1; 8/11; 8/32
[51] Int. Cl.² ............................................ A61K 7/13
[58] Field of Search............................. 8/10.2, 11, 32

[56] References Cited
UNITED STATES PATENTS

| | | | |
|---|---|---|---|
| 3,337,411 | 8/1967 | Wilmsmann et al. .................. | 8/10.2 |
| 3,359,168 | 12/1967 | Brechner et al. ...................... | 8/10.2 |
| 3,415,608 | 12/1968 | Tucker.................................... | 8/10.2 |
| 3,712,158 | 1/1973 | Kalopissis et al. ..................... | 8/11 |

OTHER PUBLICATIONS
Raiford et al., J. Amer. Chem. Soc., vol. 67, pp. 878–879, (1945).
Chemical Abstracts vol. 48:7565c, (1954).

*Primary Examiner*—Jerome D. Goldberg
*Assistant Examiner*—Vera C. Clarke
*Attorney, Agent, or Firm*—Cushman, Darby & Cushman

[57] ABSTRACT

A dye composition for keratinic fibers comprising in combination
a. at least one oxidation base comprising a paraphenylenediamine, present in the form of a free base, or in the form of an acid addition salt thereof and
b. at least one coupler of the formula:

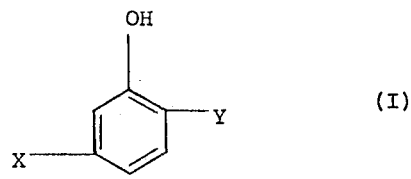

wherein Y represents a member selected from the group consisting of $-NHCOCH_3$ and $-NHCONH_2$; and X represents a member selected from the group consisting of fluorine, chlorine, and bromine, or the acid addition salt of the compound of formula (I).

15 Claims, No Drawings

DYE COMPOSITION FOR KERATINIC FIBERS CONTAINING A PHENOL COUPLER

The use in dye compositions for keratinic fibers and especially for living human hair of paraphenylenediamines is quite well known. These compounds are frequently designated as "oxidation bases" and are generally utilized in combination with compounds designated as "couplers".

These "couplers" react in an oxidizing medium with "oxidation bases" to produce dyes which impart to the fibers or to living human hair a great variety of shades, depending upon the chemical structure of the two reactants.

The choice of coupler is motivated not only by the shade desired, but also to a large extent by the degree of the stability of the shade to light and to weather.

The present invention has for an object a dye composition for keratinic fibers and in particular for living human hair, comprising, in combination:

a. at least one oxidation base comprising a paraphenylenediamine present in the form of a free base or in the form of an acid addition salt thereof; and
b. at least one coupler of the formula:

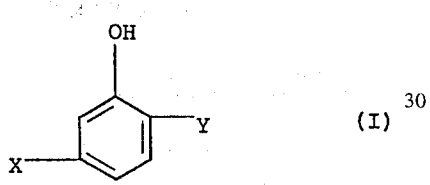

(I)

wherein Y represents a member selected from the group consisting of NHCOCH$_3$ and NHCONH$_2$ and X represents a member selected from the group consisting of fluorine, chlorine and bromine; or the acid addition salt of the compound of formula (I).

These dye compositions, wherein compound (I) is used as a coupler with a great number of paraphenylenediamines used as the oxidation base advantageously provide green or blue-green colorations, which are stable to light. The attainment of these colorations, stable to light, in oxidation dyes for keratinic fibers and living human hair provides a long sought after advantage which avoids the redness of hair after dyeing and which eliminates the red of chestnut red hair. The redness of hair after dyeing is occasioned particularly with the use as couplers of metaphenylenediamines and is in effect for the person skilled in this art highly undesirable.

Representative paraphenylenediamines usefully employed as the oxidation base in the present invention include: paraphenylenediamine, paratoluylenediamine, chloroparatoluylenediamine, methoxyparaphenylenediamine, chloroparaphenylenediamine, 2,6-dimethyl paraphenyldiamine, 2,5-dimethyl paraphenylenediamine, 2-methyl-5-methoxy paraphenylenediamine, 2,6-dimethyl-3-methoxy paraphenylenediamine, N,N-dimethyl paraphenylenediamine, 3-methyl-4-amino-N,N-diethylaniline, N,N-di-β-hydroxyethylparaphenylenediamine, 3-methyl-4-amino-N,N-di-β-hydroxyethylaniline, 3-chloro-4-amino-N,N-di-β-hydroxyethylaniline, 4-amino-N,N-(ethyl, carbamylmethyl) aniline, 3-methyl-4-amino-N,N-(ethyl, carbamylmethyl) aniline, 4-amino-N,N-(ethyl, β-piperidinoethyl) aniline, 4-amino-N,N-(ethyl, β-morpholinoethyl) aniline, 3-methyl-4-amino-N,N-(ethyl, β-morpholinoethyl) aniline, 4-amino-N,N-(ethyl, β-acetylaminoethyl) aniline, 3-methyl-4-amino-N,N-(ethyl, β-acetylaminoethyl) aniline, 4-amino-N,N-(ethyl, β-mesylaminoethyl) aniline, 3-methyl-4-amino-N,N-(ethyl, β-mesylaminoethyl) aniline, 4-amino-N,N-(ethyl, β-sulfoethyl) aniline, 3-methyl-4-amino-N,N-(ethyl, β-sulfoethyl) aniline, N-[(4'-amino) phenyl] morpholine, N-[(4'-amino) phenyl] piperidine and 3-methyl-5-amino-N,N-(ethyl, β-piperidinoethyl) aniline.

These paraphenylenediamines can be introduced into the dye composition in the form of the free base or in the form of an acid addition salt, for example, the hydrochloride, hydrobromide, or sulfate thereof.

The dye compositions according to the invention are characterized by the following points:

a. they must contain at least one of the compounds of formula (I);
b. they must contain at least one paraphenylenediamine;
c. they can contain, in addition to coupler (I), other known couplers such as: resorcin, metaaminophenol, 2,4-diamino anisole, 7-hydroxyphenomorpholine, 2-methyl-5-ureido phenol, 2,6-dimethyl-5-aminophenol, 2-methyl-5-acetylaminophenol, 2,6-dimethyl-5-acetylaminophenol, 3-amino-4-methoxyphenol and pyrazolones;
d. they can contain also other oxidation bases such as: paraaminophenol, 2-methyl-4-aminophenol, 3-methyl-4-aminophenol, 2-chloro-4-aminophenol, 3-chloro-4-aminophenol, 2,6-dimethyl-4-aminophenol, 3,5-dimethyl-4-amino-phenol, 2,3-dimethyl-4-aminophenol, 2,5-dimethyl-4-aminophenol, 2,5-diaminopyridine, and 2-hydroxy-5-aminopyridine;
e. they can also contain dyes in the form of leucoderivatives, in particular diphenylamines substituted in the 4 and 4' position by NH$_2$ or OH groups as well as other various substituents on the two benzene rings, which diphenylamines on oxidation produce indamines, indoanilines or indophenols;
f. they can also contain direct dyes such as azo, anthraquinone, nitrobenzene, indamine, indoaniline, and indophenol dyes;
g. they can be utilized in the form of an aqueous or hydroalcoholic solution containing a lower alkanol, preferably ethanol or isopropanol.

The dye composition of the present invention can also contain other solvents such as glycols, for instance, butylglycol, monoethyl ester of diethylene glycol, etc., wetting or washing agents, such as the sulfates of fatty alcohols, ethanolamides of fatty acids, polyoxyethylenated fatty acids and alcohols, thickening agents such as carboxymethylcellulose, higher fatty alcohols, cosmetic polymers such as the polymers and copolymers of polyvinylpyrrolidone, acrylic acid polymers, perfumes, complexing agents, reducing agents, alkalizing agents, for example, ammonia and ethanolamines, and acidifying agents, for example, phosphoric acid, lactic acid and acetic acid.

The couplers can be used in an amount practically molar with respect to the oxidation bases. However, it is often advantageous to use an excess of the oxidation base, for example, five moles of oxidation base per mole of coupler. This does not exclude, however, the use in certain cases of an excess of coupler with respect to the oxidation base. For example, two moles of coupler per mole of oxidation base can be used. Generally the ratio of oxidation base : coupler is between about 10:1 and 1:2, preferably between 5:1 and 1:2 and more preferably about 1:1.

The concentration of the coupler (I) can vary between about 0.05–4% by weight of the total composition.

The aggregate of the oxidation bases, couplers and other dyes represents between about 0.5–5% by weight of the total weight of the composition.

The pH of the dye compositions of the present invention can vary between 5 to 11, and preferably between 8 to 10.

The dye compositions, according to the invention, are used in the conventional manner. Thus after addition of an oxidizing agent to the composition, the resulting mixture is applied to the hair and is permitted to remain in contact therewith for a period of about 10 to 30 minutes, at ambient temperature, or a temperature between 15°–35°C. Thereafter, the hair is rinsed, washed and dried.

The oxidizing agent employed most often is $H_2O_2$ although other oxidizing agents such as urea peroxide and persalts, for example, alkaline persulfates and perborates can also be used.

The following examples illustrate the present invention. Unless otherwise stated all parts and percentages are by weight.

EXAMPLE 1

The following dye composition is prepared:

| | |
|---|---|
| 3-methyl-4-amino-N,N-(ethyl, β-mesylamino ethyl) aniline | 0.40 g |
| 3-chloro-6-acetylaminophenol | 0.46 g |
| Ethanol (95°) | 50.0 g |
| Triethanolamine, q.s.p. | pH = 8 |
| Water, q.s.p. | 100.0 g |

To this solution there are added 75 g of $H_2O_2$ (20 volumes). The resulting mixture is then applied for a period of 15 minutes at ambient temperature to bleached hair. After rinsing and shampooing there is obtained an intense emerald green coloration.

EXAMPLE 2

The following dye composition is prepared:

| | |
|---|---|
| Dihydrochloride of 2-methyl-5-methoxy paraphenylenediamine | 0.56 g |
| 3-chloro-6-ureido phenol | 0.47 g |
| Ethanol (95°) | 20.0 g |
| Triethanolamine, q.s.p. | pH = 9 |
| Water, q.s.p. | 100.0 g |

To this solution there are added 100 g of a 10% urea peroxide solution. The resulting mixture is then applied for a period of 20 minutes at 30°C to 95% naturally white hair. After rinsing and shampooing there is obtained a silvery almond-green coloration.

EXAMPLE 3

The following dye composition is prepared:

| | |
|---|---|
| Dihydrochloride of 2,6-dimethyl-3-methoxy paraphenylenediamine | 1.19 g |
| 3-chloro-6-acetylaminophenol | 1.20 g |
| Ammonia (22° Be) q.s.p. | pH = 10 |
| Water, q.s.p. | 100.0 g |

To this dye solution there is added an equal weight of $H_2O_2$ (20 volume). The resulting mixture is then applied for a period of 25 minutes at 20°C to bleached hair. After rinsing and shampooing there is obtained a very luminous emerald green coloration.

EXAMPLE 4

The following dye composition is prepared:

| | |
|---|---|
| Dihydrochloride of methoxy-paraphenylenediamine | 0.52 g |
| 3-chloro-6-acetylaminophenol | 1.38 g |
| Diethanolamide of fatty acids of coprah | 10.0 g |
| Ammonia (22° Be) q.s.p. | pH = 9 |
| Water, q.s.p. | 100.0 g |

To this dye solution there are added 25 g of $H_2O_2$ (20 volumes). The resulting mixture is then applied for a period of 15 minutes of 20°C to bleached hair. After rinsing and shampooing there is obtained a pale blue-green coloration.

EXAMPLE 5

| | |
|---|---|
| Paraaminophenol | 0.50 g |
| Dihydrochloride of 2,6-dimethyl-3-methoxy paraphenylenediamine | 1.15 g |
| 3-chloro-6-acetylaminophenol | 0.50 g |
| 7-hydroxy phenomorpholine | 0.40 g |
| Ethanol (95°) | 30.0 g |
| Ammonia (22° Be) q.s.p. | pH = 9.5 |
| Water, q.s.p. | 100.0 g |

To this solution there are added 70 g of $H_2O_2$ (20 volumes). The resulting mixture is then applied for a period of 20 minutes at ambient temperature to 95% naturally white hair. After rinsing and shampooing, there is obtained a metallic yellow-green coloration.

EXAMPLE 6

The following dye composition is prepared:

| | |
|---|---|
| Dihydrochloride of paraphenylenediamine | 1.35 g |
| 3-chloro-6-ureido phenol | 0.46 g |
| Carboxymethylcellulose | 10.0 g |
| Triethanolamine, q.s.p. | pH = 7.5 |
| Water, q.s.p. | 100.0 g |

To this solution there are added 40 g of $H_2O_2$ (20 volumes). The resulting mixture is then applied for a period of 15 minutes at 25°C to 95% naturally white hair. After rinsing and shampooing, there is obtained a violet blue-black coloration.

EXAMPLE 7

The following dye composition is prepared:

| | |
|---|---|
| Dihydrochloride of 2,6-dimethyl-3-methoxy paraphenylenediamine | 1.19 g |
| 3-chloro-6-acetylaminophenol | 0.93 g |
| Ammonium alkyl sulphate, wherein the alkyl moiety comprises 70% $C_{12}$ and 30% $C_{14}$, non-oxyethylenated | 15.0 g |
| Lauryl alcohol oxyethylenated with 10.5 moles of ethylene oxide | 10.0 g |
| Ammonia (22° Be) | 10.0 g |
| Water, q.s.p. | 100.0 g |

To this solution which has a pH of 10, there are added 100 g of $H_2O_2$ (20 volumes). The resulting mixture is then applied to hair which has a naturally red chestnut coloration for a period of 5 minutes at 35°C. After rinsing and shampooing, there is obtained a deep bronze coloration.

EXAMPLE 8

The following dye composition is prepared:

| | |
|---|---|
| Dihydrochloride of paraphenylenediamine | 1 g |
| 3-chloro-6-ureido phenol | 0.46 g |
| 7-hydroxy phenomorpholine | 0.40 g |
| N-[(4'-hydroxy-3',5'-dimethyl) phenyl]-2,6-dimethyl benzoquinoneimine | 0.30 g |
| Nitroparaphenylenediamine | 0.10 g |
| Lauryl alcohol oxyethylenated with 10.5 moles of ethylene oxide | 5 g |
| Butylglcyol | 5 g |
| Ammonia (22° Be) q.s.p. | pH = 9.7 |
| Water, q.s.p. | 100 g |

To this solution there are added 70 g of $H_2O_2$ (20 volumes). The resulting mixture is then applied for a period of 20 minutes at 25°C to 95% naturally white hair. After rinsing and shampooing, there is obtained a bronze-green coloration with golden glints.

EXAMPLE 9

The following dye composition is prepared:

| | |
|---|---|
| Dihydrochloride of 2,5-dimethyl paraphenylenediamine | 1 g |
| 3-chloro-4-aminophenol | 0.30 g |
| 3-chloro-6-acetylaminophenol | 0.1 g |
| Resorcin | 0.4 g |
| Ammonium lauryl sulfate with 19% of the starting alcohol being oxyethylenated | 20 g |
| Ethylenediamine tetraacetic acid | 0.2 g |
| Ammonia (22° Be) q.s.p. | pH = 9 |
| Water, q.s.p. | 100 g |

To this solution there are added 100 g of $H_2O_2$ (20 volumes). The resulting mixture is then applied for a period of 15 minutes at 20°C to 95% naturally white hair. After rinsing and shampooing there is obtained a light bronze coloration with golden glints.

EXAMPLE 10

The following dye composition is prepared:

| | |
|---|---|
| Sulfate of N-[(4'-amino) phenyl] piperidine | 0.88 g |
| 3-chloro-6-ureido phenol | 0.75 g |
| Ethanol (95°) | 50 g |
| Water, q.s.p. | 100 g |
| Ammonia (22° Be) q.s.p. | pH = 6.5 |

To this solution there are added 50 g of $H_2O_2$ (20 volumes). The resulting mixture is then applied for a period of 20 minutes at 30°C to 95% naturally white hair. After rinsing and shampooing, there is obtained a blue-gray coloration.

EXAMPLE 11

The following dye composition is prepared:

| | |
|---|---|
| Dihydrochloride of paraphenylenediamine | 0.22 g |
| Dihydrochloride of 2,5-diamino pyridine | 0.45 g |
| 3-chloro-6-ureido phenol | 0.92 g |
| Lauryl alcohol oxyethylenated with 10.5 moles of ethylene oxide | 5 g |
| Butylglycol | 5 g |
| Ammonia (22° Be) q.s.p. | pH = 9 |
| Water, q.s.p. | 100 g |

To this solution there are added 100 g of $H_2O_2$ (20 volumes). The resulting mixture is then applied for a period of 20 minutes at ambient temperature to bleached hair. After rinsing and shampooing there is obtained a deep violet gray coloration.

EXAMPLE 12

The following dye composition is prepared:

| | |
|---|---|
| Dihydrochloride of 2,6-dimethyl-3-methoxy paraphenylene | 0.47 g |
| 3-chloro-6-acetylaminophenol | 0.37 g |
| N-[(4'-amino) phenyl]-2-methyl-5-amino benzoquinoneimine | 0.1 g |
| Sodium lauryl sulfate with 19% of the starting alcohol being oxyethylenated | 20 g |
| Ethylenediamine tetraacetic acid | 0.2 g |
| Sodium bisulfite (40% solution) | 1 g |
| Ammonia (22° Be) | 10 g |
| Water, q.s.p. | 100 g |

By the term "sodium lauryl sulfate with 19% of the starting alcohol being oxyethylenated" is meant a mixture containing 19% lauryl alcohol oxyethylenated with 2 moles of ethylene oxide and 81% of the sodium sulfate salt of the same oxyethylenated alcohol. The pH of the above solution is equal to 10.4. To this solution there is added an equal volume of $H_2O_2$ (20 volumes). The resulting mixture is then applied for a period of 25 minutes at 25°C to bleached hair. After rinsing and shampooing there is obtained a pearly rose beige coloration.

EXAMPLE 13

The following dye composition is prepared:

| | |
|---|---|
| Paratoluylenediamine | 0.50 g |
| 3-chloro-6-acetylaminophenol | 0.46 g |
| Ammonia (22° Be) q.s.p. | pH = 9.5 |
| Water, q.s.p. | 100 g |

To this solution there is added an equal weight of $H_2O_2$ (20 volumes). The resulting mixture is then applied to 95% naturally white hair for a period of 20 minutes at ambient temperature. After rinsing and shampooing there is obtained an intense blue petroleum coloration.

EXAMPLE 14

The following dye composition is prepared:

| | |
|---|---|
| N-[(4'-amino) phenyl] morpholine | 0.75 g |
| 3-chloro-6-acetylaminophenol | 0.78 g |
| Lauryl alcohol oxyethylenated with 10.5 moles of ethylene oxide | 5 g |
| Ammonia (22° Be) q.s.p. | pH = 10.5 |
| Water, q.s.p. | 100 g |

To this solution there are added 100 g of a 10% urea peroxide solution. The resulting mixture is then applied for a period of 20 minutes at ambient temperature to bleached hair. A very light silvery blue-gray coloration is obtained.

EXAMPLE 15

The following dye composition is prepared:

| | |
|---|---|
| Dihydrochloride of 2,6-dimethyl paraphenylenediamine | 0.52 g |
| 3-chloro-6-ureido phenol | 0.47 g |
| Polymer of acrylic acid (molecular weight between about 2-3 million) | 3 g |
| Water, q.s.p. | 100 g |
| Ammonia (22° Be) q.s.p. | pH = 9 |

To this solution there is added an equal weight of $H_2O_2$ (20 volumes). The resulting mixture is then applied for a period of 20 minutes at ambient temperature to 95% naturally white hair. After rinsing and shampooing there is obtained an almond-green coloration.

EXAMPLE 16

The following dye composition is prepared:

| | |
|---|---|
| Dihydrochloride of 2,6-dimethyl-3-methoxy paraphenylenediamine | 1.18 g |
| 3-chloro-6-acetylaminophenol | 0.92 g |
| 1-γ-aminopropylamino anthraquinone | 0.15 g |
| Nitrometaphenylenediamine | 0.05 g |
| Lauryl alcohol oxyethylenated with 10.5 moles of ethylene oxide | 5 g |
| Butylglycol | 5 g |
| Ammonia (22° Be) q.s.p. | pH = 9.5 |
| Water, q.s.p. | 100 g |

To this solution there are added 60 g of $H_2O_2$ (20 volumes). The resulting mixture is then applied for a period of 25 minutes at 25°C to 95% naturally white hair. After rinsing and shampooing there is obtained a coppery blond coloration with rose glints.

EXAMPLE 17

The following dye composition is prepared:

| | |
|---|---|
| 3-methyl-4-amino-N,N-(ethyl, sulfoethyl) aniline | 1.95 g |
| 3-chloro-6-ureido phenol | 1.40 g |
| Ethanol (95°) | 30 g |
| Water, q.s.p. | 100 g |
| Ammonia (22° Be) q.s.p. | pH = 9.5 |

To this solution there are added 50 g of $H_2O_2$ (20 volumes). The resulting mixture is then applied for a period of 25 minutes at ambient temperature to 95% naturally white hair. After rinsing and shampooing, there is obtained a pale pearly emerald green coloration.

EXAMPLE 18

The following dye composition is prepared:

| | |
|---|---|
| 4-amino-N,N-di-β-hydroxyethyl aniline | 0.49 g |
| 3-chloro-6-acetylaminophenol | 0.47 g |
| Ammonium lauryl sulfate | 10 g |
| Water, q.s.p. | 100 g |
| Ammonia (22° Be) q.s.p. | pH = 9.5 |

To this solution there are added 80 g of $H_2O_2$ (20 volumes). The resulting mixture is then applied for a period of 20 minutes at ambient temperature to 95% naturally white hair. After rinsing and shampooing there is obtained an emerald green coloration.

EXAMPLE 19

The following dye composition is prepared:

| | |
|---|---|
| Trihydrochloride of 4-amino-N,N-(ethyl, β-piperidinoethyl) aniline | 1.45 g |
| 3-chloro-6-ureido phenol | 0.56 g |
| Ethanol (95°) | 50 g |
| Ammonia (22° Be) q.s.p. | pH = 6.5 |
| Water, q.s.p. | 100 g |

To this solution there are added 100 g of $H_2O_2$ (20 volumes). The resulting mixture is then applied to naturally white hair for a period of 20 minutes at ambient temperature. After rinsing and shampooing there is obtained a silvery blue-green coloration.

EXAMPLE 20

The following dye composition is prepared:

| | |
|---|---|
| 4-amino-N,N-(ethyl, carbamylmethyl) aniline | 0.77 g |
| 3-chloro-6-acetylaminophenol | 0.74 g |
| Lauryl alcohol oxyethylenated with 10.5 moles of ethylene oxide | 5 g |
| Butylglycol | 5 g |
| Ammonia (22° Be) q.s.p. | pH = 7.5 |
| Water, q.s.p. | 100 g |

To this solution there is added an equal weight of $H_2O_2$ (20 volumes). The resulting mixture is then applied for a period of 25 minutes at ambient temperature to 95% naturally white hair. After rinsing and shampooing, there is obtained a silvery gray-green coloration.

EXAMPLE 21

The following dye composition is prepared:

| | |
|---|---|
| Dihydrochloride of para-toluylenediamine | 0.30 g |
| 3-chloro-6-ureido phenol | 0.46 g |
| 2-amino-4-hydroxy-5-methyl-4'-amino diphenylamine | 0.30 g |
| Butylglycol | 5 g |
| Lauryl alcohol oxyethylenated with 10.5 moles of ethylene oxide | 5 g |
| Ammonia (22° Be) q.s.p. | pH = 9 |
| Water, q.s.p. | 100 g |

To this solution there is added an equal weight of $H_2O_2$ (20 volumes). The resulting mixture is then applied for a period of 20 minutes at ambient temperature to 95% naturally white hair. After rinsing and shampooing, there is obtained a silvery mauve-gray coloration.

EXAMPLE 22

The following dye composition is prepared:

| | |
|---|---|
| Dihydrochloride of para-toluylenediamine | 0.58 g |
| 3-chloro-6-ureido phenol | 0.37 g |
| Ethanol (95°) | 50 g |
| Triethanolamine, q.s.p. | pH = 5 |
| Water, q.s.p. | 100 g |

To this solution there are added 50 g of $H_2O_2$ (20 volumes). The resulting mixture is then applied for 5 minutes at ambient temperature to bleached hair. After rinsing and shampooing, there is obtained a silvery blue-gray coloration.

EXAMPLE 23

The following dye composition is prepared:

| Dihydrochloride of para- | |
|---|---|
| toluylenediamine | 0.48 g |
| 3-chloro-6-acetylaminophenol | 0.46 g |
| Ammonium lauryl sulfate wherein 19% of the starting alcohol is oxyethylenated | 20 g |
| Ethylenediamine tetraacetic acid | 0.2 g |
| Sodium bisulfite (40% solution) | 1 g |
| Ammonia (22° Be) | 10 g |
| Water, q.s.p. | 100 g |

To this solution having a pH of 11 there is added an equal weight of H₂O₂ (20 volumes). The resulting mixture is then applied for a period of 20 minutes at ambient temperature to 95% naturally white hair. After rinsing and shampooing, there is obtained an olive-green coloration.

EXAMPLE 24

The following dye composition is prepared:

| Monohydrochloride of 3-methyl- | |
|---|---|
| 4-amino-N,N-diethylaniline | 0.65 g |
| 3-chloro-6-acetylaminophenol | 0.55 g |
| Quaternary copolymer of polyvinylpyrrolidone (average molecular weight 100,000) sold under the trademark GAFQUATE 734 | 7 g |
| Ethanol (95°) | 30 g |
| Triethanolamine, q.s.p. | pH = 8.5 |
| Water, q.s.p. | 100 g |

To this solution there are added 100 g of a 10% urea peroxide solution. The resulting mixture is then applied for a period of 20 minutes at ambient temperature to 95% naturally white hair. After rinsing and shampooing, there is obtained a tin-gray coloration.

EXAMPLE 25

The following dye composition is prepared:

| Dihydrochloride of para- | |
|---|---|
| toluylenediamine | 1 g |
| Paraaminophenol | 0.27 g |
| 3-chloro-6-ureido phenol | 0.47 g |
| 3-chloro-6-acetaminophenol | 0.47 g |
| Hydrochloride of 4-hydroxy-N,N-dimethylamino-4'-diphenylamine | 0.20 g |
| Ammonium lauryl sulfate | 10 g |
| Water, q.s.p. | 100 g |
| Triethanolamine, q.s.p. | pH = 8 |

To this solution there is added an equal weight of H₂O₂ (20 volumes). The resulting mixture is then applied for a period of 20 minutes at 20°C to 95% naturally white hair. After rinsing and shampooing, there is obtained a very deep chestnut coloration, with bronze-green glints.

EXAMPLE 26

The following dye composition is prepared:

| 4-amino-N,N-(ethyl, carbamylmethyl) aniline | 0.29 g |
|---|---|
| 3-chloro-6-ureido phenol | 0.23 g |
| Butylglycol | 3 g |
| Lauryl alcohol oxyethylenated with 10.5 moles of ethylene oxide | 5 g |
| Triethanolamine, q.s.p. | pH = 5.8 |
| Water, q.s.p. | 100 g |

To this solution there are added 75 g of H₂O₂ (20 volumes). The resulting mixture is then applied for a period of 10 minutes at ambient temperature to bleached hair. After rinsing and shampooing, there is obtained a silvery blue-gray coloration.

EXAMPLE 27

The following dye composition is prepared:

| Dihydrochloride of para- | |
|---|---|
| toluylenediamine | 0.49 g |
| 3-chloro-6-ureido phenol | 0.47 g |
| Water, q.s.p. | 100 g |
| Ammonia (22° Be) q.s.p. | pH = 10.5 |

To this solution there are added 100 g of a 1.1% ammonium persulfate solution. The resulting mixture is then applied for a period of 20 minutes at ambient temperature to 95% naturally white hair. After rinsing and shampooing, there is obtained a silvery blue-green coloration.

EXAMPLE 28

The following dye composition is prepared:

| 3-methyl-4-amino-N,N- (ethyl, carbamylmethyl) aniline | 1.02 g |
|---|---|
| 3-chloro-6-ureido phenol | 3.72 g |
| Butylglycol | 3 g |
| Lauryl alcohol oxyethylenated with 10.5 moles of ethylene oxide | 5 g |
| Ammonia (22° Be) q.s.p. | pH = 10 |
| Water, q.s.p. | 100 g |

To this solution there is added an equal weight of H₂O₂ (20 volumes). The resulting mixture is then applied for a period of 15 minutes at ambient temperature to bleached hair. After rinsing and shampooing there is obtained a very intense emerald green coloration.

What is claimed is:

1. A dye composition for keratinic fibers comprising an aqueous or hydroalcoholic solution of
   a. at least one oxidation base comprising a paraphenylenediamine, present in the form of a free base, or in the form of an acid addition salt thereof and
   b. at least one coupler of the formula:

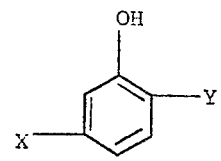

[(I)]

wherein Y represents a member selected from the group consisting of —NHCOCH₃ and —NHCONH₂; and X represents a member selected from the group consisting of fluorine, chlorine, and bromine, or the acid addition salt of said coupler, said coupler being present in an amount of 0.05 to 4% based on the total weight of the composition and the molar ratio of said oxidation base to said coupler being between 5:1 and 1:2.

2. The composition of claim 1 wherein said paraphenylenediamine is selected from the group consisting of: paraphenylenediamine, paratolylenediamine, chloroparatoluenediamine, methoxyparaphenylenediamine, chloroparaphenylenediamine, 2,6-dimethyl paraphenylenediamine, 2,5-dimethyl paraphenylenediamine, 2-methyl-5-methoxy paraphenylenediamine, 2,6-dimethyl-3-methoxy paraphenylenediamine, N,N-dimethyl paraphenylenediamine, 3-methyl-4-amino- N,N-diethylaniline, N,N-di-β-hydroxyethylparaphenylenediamine, 3-methyl-4-amino-N,N-di-β-hydroxyethylaniline, 3-chloro-4-amino-N,N-di-β-hydroxyethylaniline, 4-amino-N,N-(ethyl, carbamylmethyl) aniline, 3-methyl-4-amino-N,N-(ethyl, carbamylmethyl) aniline, 4-amino-N,N-(ethyl, β-piperidinoethyl) aniline, 4-amino-N,N-(ethyl, β-morpholinoethyl) aniline, 3-methyl-4amino-N,N-(ethyl, β-morpholinoethyl) aniline, 4-amino-N,N-(ethyl, β-acetylaminoethyl) aniline, 3-methyl-4-amino-N,N-(ethyl, β-acetylaminoethyl) aniline, 4-amino-N,N-(ethyl, β-mesylaminoethyl) aniline, 3-methyl-4-amino-N,N-(ethyl, β-mesylaminoethyl) aniline, 4-amino-N,N-(ethyl, β-sulfoethyl) aniline, 3-methyl-4-amino-N,N-(ethyl, β-sulfoethyl) aniline, N-[(4'-amino) phenyl] morpholine, N-[(4'-amino) phenyl] piperidine and 3-methyl-5-amino-N,N-(ethyl, β-piperidinoethyl) aniline.

3. The composition of claim 1 which also includes in addition to said paraphenylenediamine at least one other oxidation base.

4. The composition of claim 3 wherein said other oxidation base is selected from the group consisting of a paraaminophenol and a heterocyclic base.

5. The composition of claim 4 wherein said heterocyclic base is selected from the group consisting of 2,5-diamino pyridine.

6. The composition of claim 1 which also includes at least one addititonal coupler.

7. The composition of claim 6 wherein said additional coupler is selected from the group consisting of resorcin, metaaminophenol, 2,4-diamino anisole, 7-hydroxy phenomorpholine, 2-methyl-5-ureido phenol, 2,6-dimethyl-5-aminophenol, 2-methyl-5-acetylaminophenol, 3-amino-4-methoxy phenol, 2,6-dimethyl-5-acetylaminophenol and a pyrazolone.

8. The composition of claim 1 which also includes a dye selected from the group consisting of anthraquinone, nitrobenzene, indamine, indophenol and indoaniline dye.

9. The composition of claim 1 which also includes a leucoderivative of an indamine, a leucoderivative of an indophenol, or a leucoderivative of an indoaniline.

10. The composition of claim 1 wherein said hydroalcoholic solution contains a lower alkanol.

11. The composition of claim 1 which also contains one or more of a glycol, a wetting agent, a thickening agent, a vinyl pyrrolidone polymer, an acrylic acid polymer, a complexing agent and a reducing agent.

12. The composition of claim 1 having a pH between 5 to 11.

13. A process for dyeing human hair consisting essentially of applying an effective amount of a mixture of an oxidizing agent and the dye composition of claim 1 to the hair and rinsing, washing and drying the hair.

14. The process of claim 13 wherein said oxidizing agent is selected from the group consisting of hydrogen peroxide, urea peroxide, and a persalt.

15. The process of claim 14 wherein said persalt is an alkaline persulfate or perborate.

* * * * *